US006164968A

United States Patent [19]

Feine

[11] Patent Number: 6,164,968

[45] Date of Patent: Dec. 26, 2000

[54] TRIMODULAR ULTRASONIC DENTAL DEVICE

[76] Inventor: James Feine, P.O. Box 2009, Bellaire, Tex. 77402-2009

[21] Appl. No.: 09/086,142

[22] Filed: May 28, 1998

Related U.S. Application Data

[60] Provisional application No. 60/047,840, May 28, 1997.

[51] Int. Cl.$^{7}$ ....... A61C 1/07

[52] U.S. Cl. ....... 433/119; 433/86

[58] Field of Search ....... 433/86, 119

[56] References Cited

U.S. PATENT DOCUMENTS

| | | | |
|---|---|---|---|
| Re. 25,033 | 8/1961 | Balamuth et al. | 433/119 |
| 2,680,333 | 6/1954 | Calosi | 433/119 |
| 2,831,132 | 5/1958 | Jackson | 310/26 |
| 2,947,082 | 8/1960 | Epstein | 433/119 |
| 3,133,351 | 5/1964 | Von Seggern | 433/119 |
| 3,488,851 | 1/1970 | Haydu | 433/86 |
| 3,526,036 | 9/1970 | Goof | 433/119 |
| 3,589,012 | 6/1971 | Richman | 433/86 |
| 3,645,255 | 2/1972 | Robinson | 433/119 |
| 3,654,502 | 4/1972 | Carmona et al. | 433/119 |
| 3,930,173 | 12/1975 | Banko | 433/119 |
| 4,283,174 | 8/1981 | Sertich | 433/119 |
| 4,333,197 | 6/1982 | Kuris | 433/119 |
| 4,370,131 | 1/1983 | Banko | 433/119 |
| 4,818,229 | 4/1989 | Vasile | 433/127 |
| 4,820,152 | 4/1989 | Warrin et al. | 433/86 |
| 4,961,698 | 10/1990 | Volck | 433/86 |
| 5,059,122 | 10/1991 | Hetzel | 433/118 |
| 5,106,302 | 4/1992 | Farzom-Nia et al. | 433/219 |
| 5,749,727 | 5/1998 | Dao et al. | 433/119 |
| 5,775,901 | 7/1998 | Riso | 433/119 |

*Primary Examiner*—John J. Wilson
*Attorney, Agent, or Firm*—Daniel N. Lundeen

[57] ABSTRACT

A three-part ultrasonic dental insert and replacement system used in a handpiece having an induction coil disposed about a well and operably connected to power supply. The three parts include a magnetostrictive element, a velocity transducer and a tip. The magnetostrictive element has a crown at one end which is releasably attached to a distal end of the velocity transducer. The tip is releasably attached to a proximal end of the velocity transducer. The insert can comprise a set of interchangeable tips wherein the velocity transducer and the tips are ultrasonically operable with the coil and the magnetostrictive element. The three-part replacement system comprises a set of the magnetostrictive coils and a set of the velocity transducer elements, as well as the interchangeable tips. The velocity transducer and tip sets include a plurality of transducer-tip combinations ultrasonically operable at the ultrasonic frequencies of the magnetostrictive elements.

23 Claims, 2 Drawing Sheets

TRIMODULAR ULTRASONIC DENTAL DEVICE

CROSS REFERENCE TO RELATED APPLICATION

This application claims the benefit of provisional application U.S. Ser. No. 60/047,840 filed May 28,1997.

FIELD OF THE INVENTION

This invention relates to ultrasonic dental instruments, and more particularly to a three-part ultrasonic dental insert for an ultrasonic handpiece.

BACKGROUND OF THE INVENTION

Ultrasonic dental scalers and surgical instruments are available from several different suppliers. These units generally have a power supply unit and a handpiece connected to the power supply by a cable by which electrical current and water are typically supplied to the handpiece. The handpiece includes a tip insert which has a transducer stack which interacts with an alternating magnetic field created by a coil in a wall of the housing to set up an ultrasonic vibration of the insert. The insert generally has a dental tool or tip which is integral with the transducer stack or removably attached thereto.

In this prior art design, the insert and tip are removable from the handpiece for sterilization in an autoclave. When the tip or transducer stack fail or wear sufficiently to be replaced, this is done by replacing the entire insert in the case of the integral stack and tip insert, or by replacement of the stack or the tip as necessary in the two-part insert system. The transducer stacks and tips, as well as the complete insert, can be expensive to replace, particularly where the insert comprising the transducer stack and tip is a one-piece insert.

Some manufacturers provide a variety of tips which can be used with the same transducer stack and handpiece. This provides versatility in that the ultrasonic dental tool can be used for different purposes or operating conditions. However, one manufacturer's tips are not generally interchangeable with another manufacturer's. This is due, not only to the different connection between the tip and stack which may be employed, but also because of the different operating frequencies which are employed. The nature of ultrasonics requires that the tip be matched with the transducer stack so that the end of the tip corresponds to a node of maximum vibration, whereas the connection of the transducer stack to the handpiece must correspond to an antinode where there is little or no vibration which would otherwise generate heat and ultimately result in a failure of the connection. Since changing the length or the operating frequency will change the location of the nodes, and of the antinodes, the interchangeability of the tips between different manufacturers is problematic.

Applicant has found that it would be desirable to reduce the cost of replacing broken or worn components of an ultrasonic dental insert. Applicant has further found that it would also be desirable to be able to interchangeably use tips and transducer stacks in different handpieces of different manufacturers.

SUMMARY OF THE INVENTION

The present invention is directed to a three-part ultrasonic dental insert used in a handpiece of an ultrasonic dental tool. By providing the dental insert as a three-part unit, the various parts can be made interchangeable from one insert to another. In addition, the three-part assembly allows the replacement of broken or worn components individually, rather than as a complete unit.

In one aspect, the present invention provides a three-part ultrasonic dental insert for use in a handpiece having an induction coil disposed about a well and operably connected to a power supply. The dental insert comprises a magnetostrictive element, a velocity transducer and a tip. The magnetostrictive element has a crown at one end and the other end is adapted to be received in the well of the handpiece. The magnetostrictive element has a magnetostrictive frequency matching the coil and power supply. The velocity transducer has proximal and proximal ends. The proximal end is releasably attached to the crown of the magnetostrictive element. The tip has a proximal end releasably secured to the distal end of the velocity transducer. The velocity transducer and the tip are ultrasonically operable with the coil and magnetostrictive element.

As used herein, the term "ultrasonically operable" means that the components are matched for ultrasonic operation at the frequency of the coil/magnetostrictive element, i.e. the distal end of the tip corresponds to a node and the insert includes an antinode, at or near which the insert can be secured to the handpiece, at the operating frequency of the coil/magnetostrictive element.

In another aspect, the present invention provides a three-part ultrasonic dental insert for use in a handpiece having an induction coil disposed about a well and operably connected to a power supply. The three-part ultrasonic dental insert comprises a magnetostrictive element, a velocity transducer releasably attached to the magnetostrictive element, and a set of interchangeable tips. Each tip has a distal end releasably attachable to the distal end of the velocity transducer. The velocity transducer and the tips are ultrasonically operable with the coil, the power supply and the magnetostrictive element.

In yet another aspect, the present invention provides a three-part replacement system for repairing ultrasonic dental inserts for use in handpieces having an induction coil disposed about a well and operably connected to a power supply. The replacement system comprises a set of magnetostrictive elements, a set of velocity transducers and a set of interchangeable tips. The magnetostrictive elements have a crown at one end and are receivable in the well of the handpiece. The set of magnetostrictive elements includes at least two elements having different magnetostrictive frequencies to match coils operable at different frequencies. The velocity transducers have proximal and distal ends. The distal ends of the velocity transducers are releasably attachable to the crowns of the magnetostrictive elements. The tips have distal ends releasably attachable to the distal ends of the velocity transducers. The velocity transducer and tip sets include a plurality of transducer-tip combinations ultrasonically operable at the ultrasonic frequencies of the magnetostrictive elements. The set of velocity transducers preferably includes at least one velocity transducer matched for interchangeable operation at different ultrasonic frequencies with at least two different magnetostrictive elements. The interchangeably operable velocity transducers are preferably operable at ultrasonic frequency pairs selected from the group consisting of: about 18 kHz and about 18.8 kHz; about 25 kHz and about 30 kHz; and the like. The set of tips preferably includes a plurality of tips operable with a plurality of velocity transducers for operation at different ultrasonic frequencies.

BRIEF DESCRIPTION THE DRAWINGS

DETAILED DESCRIPTION OF THE INVENTION

Figure 1:
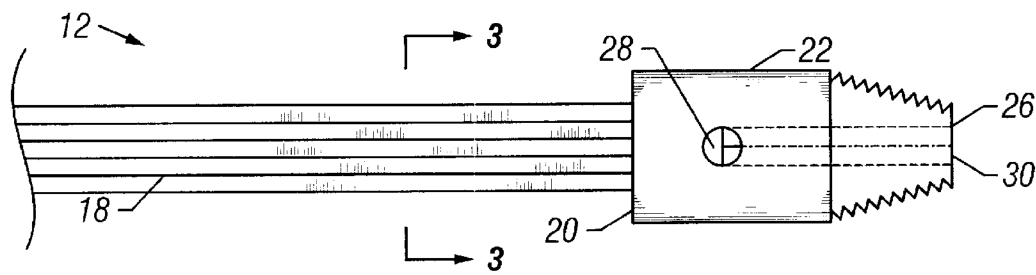
FIG. 1 is a longitudinal section of a stack section of a trimodular ultrasonic dental device according to the present invention.
Figure 2:
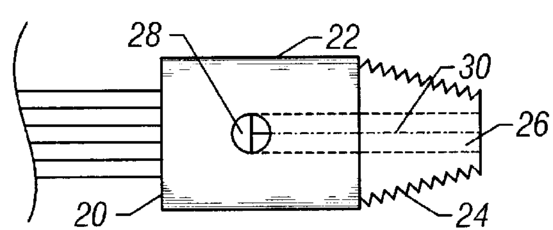
FIG. 2 is an enlarged longitudinal section of the crown or head piece used in the stack section of FIG. 1.
Figure 3:
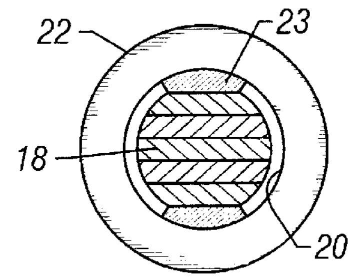
FIG. 3 is a cross section of the stack section of FIG. 1 as seen along lines 3—3.
Figure 4:
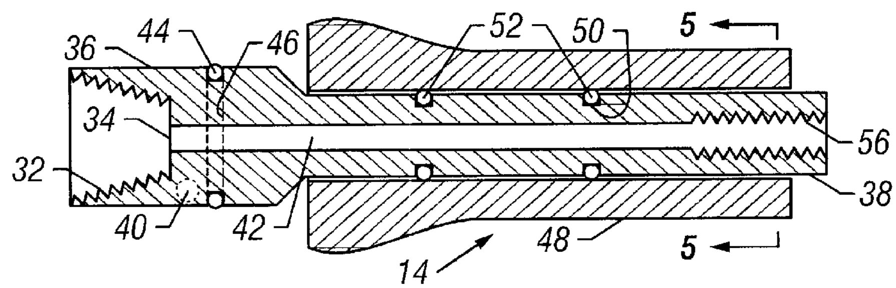
FIG. 4 is a longitudinal section of a velocity transducer section used in a trimodular ultrasonic dental device according to the present invention.
Figure 5:
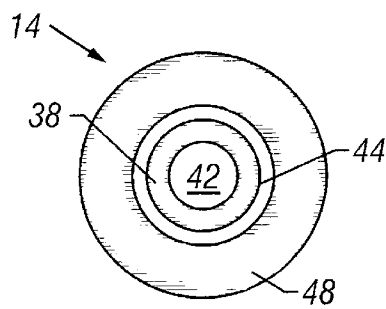
FIG. 5 is a cross-sectional view of the velocity transducer section of FIG. 4 as seen along the lines 5—5.
Figure 6:
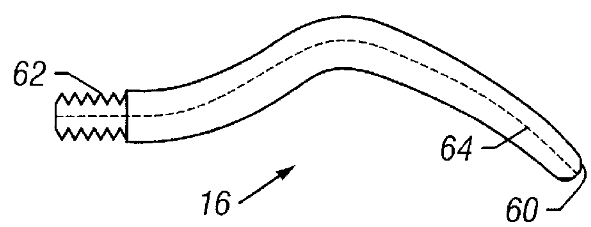
FIG. 6 is a longitudinal section of a tip used in a trimodular ultrasonic dental device according to the present invention.
Figures 7, 8:
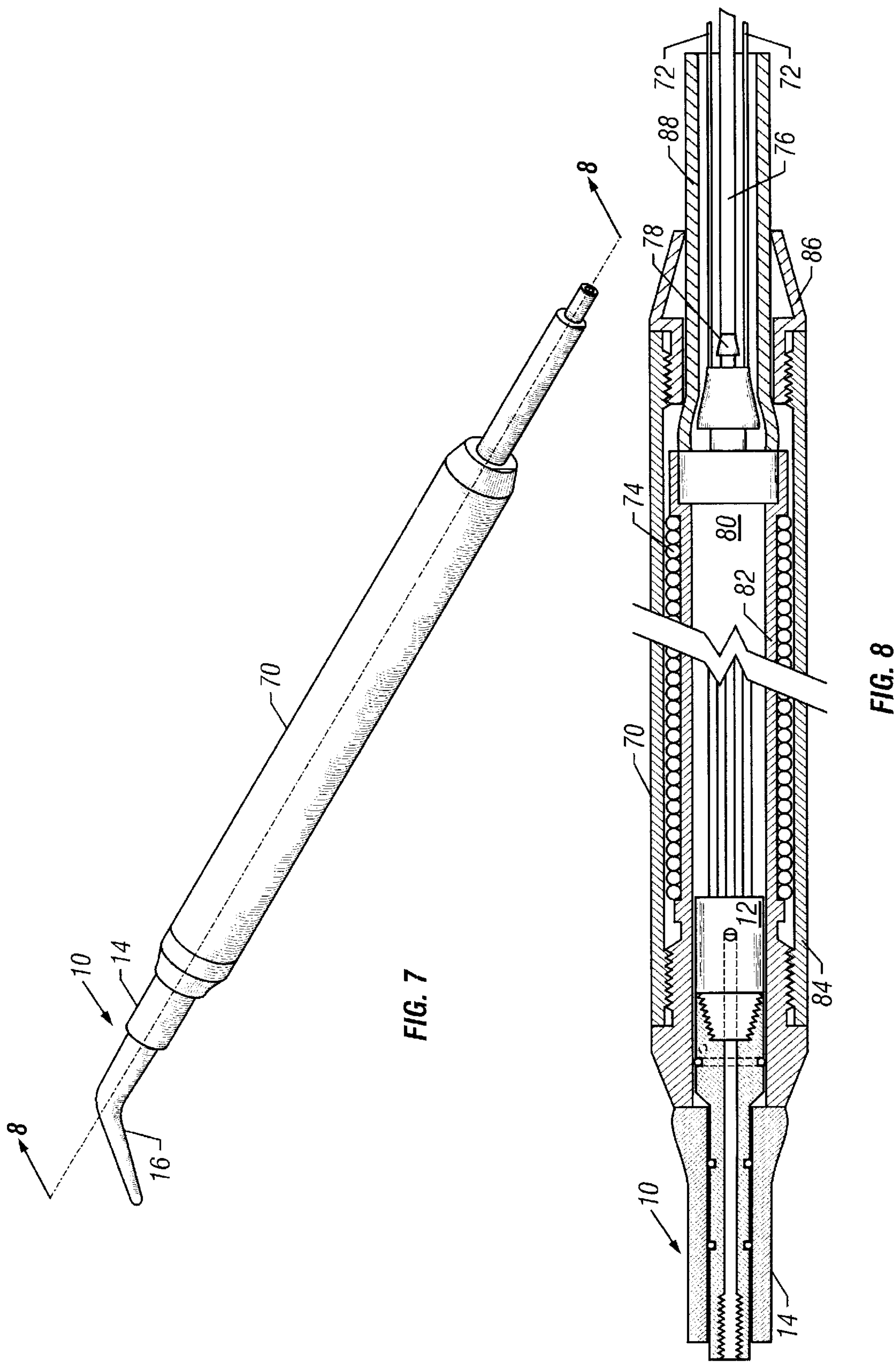
FIG. 7 is a perspective view of an assembled trimodular ultrasonic dental insert in a handpiece.
FIG. 8 is a longitudinal sectional view of a handpiece containing the insert (without the tip).

With reference to FIGS. 1–8 wherein like numerals are used to indicate like parts, the insert 10 (FIG. 7) includes a magnetostrictive element 12 (FIGS. 1–3), a velocity transducer 14 (FIGS. 4–5) and a tip 16 (FIG. 6). The magnetostrictive element 12 includes a plurality of magnetostrictive leaves 18 which are stacked together and can be secured at either end thereof as is known in the art. The magnetostictive leaves can be made of any suitable magnetostrictive material, such as, for example, nickel. The leaves 18 are preferably brazed at either end, for example, silver brazed. The distal end of the stack of magnetostrictive leaves 18 is received in a bore 20 formed in a distal end of a crown or head piece 22. The magnetostrictive leaves 18 are preferably silver brazed at 23 into the bore 20 of the head piece 22 to secure the magnetostrictive leaves 18 as a stack thereto.

The head piece 22 has a generally cylindrical outer surface and includes the bore 20 formed in the distal end thereof as previously mentioned. The proximal end of the head piece 22 can include tapered threads 24 terminating at a transverse abutment surface 26, or alternatively straight threads or a friction fit (not shown) could also be employed. The preferred tapered threads 24 are machined with rounded ends, and enhance the metal-to-metal engagement area for the transmission of vibration from the magnetostrictive element 12 to the velocity transducer 14, as described in more detail below. A transverse bore 28 is formed through the head piece 22 which serves as a water inlet port, and also to receive a tool for threadedly engaging the magnetostrictive element 12 into the velocity transducer 14. A longitudinal bore 30 is formed through the head piece 22 extending from the transverse bore 28 and opening to the abutment surface 26. The bore 30 serves as a passage for water through the head piece 22 into the velocity transducer 14.

The velocity transducer 14 has a proximal end with a tapered, threaded bore 32 and transverse abutment surface 34 for receiving the tapered threads 24 and abutment surface 26 of the head piece 22. The velocity transducer 14 includes a distal section 36 with an enlarged outside diameter, relative to an outside diameter of distal section 38, and preferably the outside diameter of the proximal section 36 matches the outside diameter of the head piece 22. A transverse bore 40 is formed through the proximal section 36 to facilitate attachment of a tool for threading the velocity transducer 14 to the head piece 22 of the magnetostrictive element 12. A central passage 42 through the velocity transducer 14 is provided for water to flow therethrough.

An O-ring 44 is received in O-ring groove 46 formed in an outer surface of the proximal section 36 to provide a friction fit of the velocity transducer 14 in the handpiece 10. The distal end 38 of the velocity transducer 14 can receive a contoured finger grip 48 which has an interior bore just slightly larger than the outside diameter of the distal section 38. The finger grip 48 can be contoured to facilitate tactile engagement, and may be made of any suitable material such as a thermoplastic or thermosetting polymer. The proximal section 38 of the velocity transducer 14 can include longitudinally spaced-apart O-ring grooves 50 which receive O-rings 52 and provide a seal with the finger grip 48 when received on the distal section 38. The finger grip 48 can also be provided with interior ribs 54 corresponding to the grooves 50 to provide a snap-on engagement of the finger grip 48 with the section 38. The O-ring grooves 46,50 can generally correspond to points of very little vibration, or antinodes, to minimize the generation of heat at these locations. The internal passage 42 terminates at threads 56 (preferably tapered) adjacent the proximal end of the section 38 for engagement of the tip 16.

The velocity transducer 14 is generally machined from thick-walled tubing of suitable autoclavable material, such as stainless steel, for example.

The tip 16 has a proximal working end 60 and a tapered threaded proximal end 62 adapted to be threadably engaged in the passage 42 by the terminal threads 56 (preferably tapered) of the velocity transducer 14. The tip 16 includes a central passage 64 for water to flow therethrough. The distal end 60 generally corresponds to a vibration node, i.e. a location at which vibratory motion is at a maximum. The tip 16 is generally manufactured from a tubing piece of the appropriate inside and outside diameters which is bent and molded into the desired shape and then hardened and polished. A stainless steel such as 420 or 440 grade is generally suitable for this purpose, but, depending on the function or purpose of the tip 16, it can also be made from titanium or other materials, and can optionally be coated with an abrasive material such as diamond. The tip 16 can be a universal tip, a left tip or a right tip, have flattened sides and a spooned end, or can be a surgical blade, or the like.

In operation, the insert 10 (FIGS. 7 and 8) is assembled for use from the desired magnetostrictive element 12, velocity transducer 14 and tip 16. The assembled insert 10 is then placed inside a suitable handpiece by frictional engagement, for example, by means of O-ring 44, and supplied with power to induce vibration of the magnetostrictive element 12. The magnetostrictive element 12 is vibrated by passing an alternating current supplied via wires 72 through coil 74 formed in the shell of the handpiece 70. Vibration is transmitted from the magnetostrictive element 12 through the velocity transducer 14 and then to the tip 16. Water is supplied to the handpiece 70 via tubing 76 and nipple fitting 78 and flows through the well 80 receiving the magnetostrictive element 12 to cool the magnetostrictive element 12, and simultaneously warm the water as it flows into the velocity transducer 14 via the passage 42, and then through the tip 16 via the passage 64. The handpiece 70 is preferably constructed from an inner cylindrical piece 82, with an inside diameter forming the well 80 and around which the wire is wrapped to form the coil 74, and an outer cylindrical piece 84 threaded to the inner cylindrical piece 82 at a distal end and threaded to engage tail nut 86 at a distal end. The water tubing 76 and wires 72 are protected in a cable sheath 88 which runs to a conventional power/water supply unit (not shown).

As the water is ejected from the distal end 60 of the tip 16, it serves as a transmission medium between the tip 16 and the surface of the tooth or tissue with which the tip 16 is being operated, and also serves to cool the tissue or tooth surface and flush away any debris or foreign material, as is known in the art.

When it is desired to use a different tip, the tip 16 is replaced with the tip of desired configuration and characteristics. When the magnetostrictive element 12 needs to be replaced, this can be done by removing the insert 10 from the handpiece and using wrenches with elongated elements to engage the respective transverse passages 28 and 40 to unthread the magnetostrictive element 12 from the velocity transducer 14. In this manner, the velocity transducer 14 can be used with a series of interchangeable tips 16, or with different magnetostrictive elements 12, for example, for use in different handpieces.

To use the trimodular insert of the present invention with a specific power supply, the dental practitioner maintains an inventory of a magnetostrictive element and a velocity transducer, perhaps with one or two replacement magnetostrictive elements and velocity transducers to use in the event of failure or while the others are being sterilized as in an autoclave, and a variety of tips. The dental practitioner can use a wide array of tips without having to purchase an entire insert for each type of tip. Moreover, the dental practitioner can simply replace the tip if it becomes worn or breaks, rather than the entire insert.

The system can also be used with different power supplies. For example, if a dental practitioner has 25 kHz and 30 kHz ultrasonic dental generators, the tips from the practitioner's set can be used with both machines by changing the magnetostrictive element, and/or the velocity transducer if the handpieces of the two (or more) machines are not compatible. In general different types of velocity transducers are used to fit the handpieces of various ultrasonic generator manufacturers.

The magnetostrictive elements and tips can be releasably attached to the velocity transducer by rolled threaded connection as described above, but the present invention also contemplates that other connection means can be suitably employed, such as, for example, collets, twist-snaps, captive nuts or the like. The velocity transducer and tips can be configured for external water flow, as well as the internal water flow illustrated above.

The above description is only illustrative of embodiments of the invention. Various changes and modifications of these embodiments will occur to the skilled artisan in view of the preceding specification. It is intended that all such modifications and changes within the scope and spirit of the appended claims be embraced thereby.

What is claimed is:

1. A three-part ultrasonic dental insert for use in a handpiece having an induction coil disposed about a well and operably connected to a power supply comprising:

a magnetostrictive element having a magnetostrictive stack brazed at one end in a bore formed in a distal end of a head piece, wherein the element is adapted to be received in the well and has a magnetostrictive frequency matching the coil and power supply;

a velocity transducer having proximal and distal ends, wherein the proximal end is releasably attached to the head piece of the magnetostrictive element;

a tip having a proximal end releasably secured to the distal end of the velocity transducer, wherein the velocity transducer and the tip are ultrasonically operable with the coil and magnetostrictive element.

2. The insert of claim 1 wherein the insert is held by a friction fit between the velocity transducer and a distal end of the handpiece.

3. The insert of claim 1 comprising a continuous passage for water through the head piece, velocity transducer and tip.

4. The insert of claim 1 wherein the head piece has tapered external threads engageable by tapered internal threads formed in the distal end of the velocity transducer.

5. The insert of claim 4 wherein the tapered threads have rounded ends.

6. The insert of claim 1 wherein the proximal end of the tip is threadably engaged with the distal end of the velocity transducer.

7. The insert of claim 1 wherein a distal end of the tip corresponds to a node of maximum vibration and attachment of the head piece to the velocity transducer corresponds to an antinode.

8. A three-part ultrasonic dental insert for use in a handpiece having an induction coil disposed about a well and operably connected to a power supply comprising:

a magnetostrictive element;

a velocity transducer element releasably attachable to the magnetostrictive element;

a set of interchangeable tips, each tip having a proximal end releasably attachable to a distal end of the velocity transducer, wherein the velocity transducer and the tips are ultrasonically operable with the coil and the magnetostrictive element, wherein a distal end of each tip corresponds to a node of maximum vibration and attachments of the velocity transducer to the magnetostrictive element and to each tip correspond to antinodes.

9. A three-part replacement system for repairing ultrasonic dental inserts for use in handpieces having an induction coil disposed about a well and operably connected to a power supply, comprising:

a set of magnetostrictive elements having a crown at one end, wherein the elements are receivable in the well of a handpiece and the set includes at least two elements having different magnetostrictive frequencies to match coils operable at different frequencies;

a set of velocity transducers having proximal and distal ends, wherein the proximal ends are releasably attachable to the crowns of the magnetostrictive elements;

a set of interchangeable tips having proximal ends releasably attachable to the distal ends of the velocity transducers, wherein the velocity transducers and the tip sets include a plurality of transducers-tip combinations ultrasonically operable at the ultrasonic frequencies of the magnetostrictive elements.

10. The replacement system of claim 9, wherein the set of velocity transducers includes at least one velocity transducer matched for interchangeable operation at different ultrasonic frequencies with at least two different magnetostrictive elements.

11. The replacement system of claim 10 wherein the set of velocity transducers includes at least two interchangeably operable velocity transducers operable at the ultrasonic frequency pair selected from the group consisting of the frequency pair of about 18 kHz and about 18.8 kHz, and the frequency pair of about 25 kHz and about 30 kHz.

12. The replacement system of claim 10 wherein the set of tips includes a plurality of tips operable with a plurality of velocity transducers for operation at different ultrasonic frequencies.

13. The replacement system of claim 12 wherein distal ends of the tips correspond to a node of maximum vibration and attachment of the crowns to the velocity transducers corresponds to an antinode.

14. The replacement system of claim 10 wherein distal ends of the tips correspond to a node of maximum vibration and attachment of the crowns to the velocity transducers corresponds to an antinode.

15. The replacement system of claim 9 wherein each insert is held by a friction fit between the velocity transducer and a distal end of the handpiece.

16. The replacement system of claim 9 comprising a continuous passage for water through the crowns, velocity transducers and tips.

17. The replacement system of claim 9 wherein each crown has tapered external threads engageable by tapered internal threads formed in the distal ends of the velocity transducers.

18. The replacement system of claim 17 wherein the tapered threads have rounded ends.

19. The replacement system of claim 9 wherein the proximal ends of the tips are threadably engageable with the distal ends of the velocity transducers.

20. The replacement system of claim 9 wherein distal ends of the tips correspond to a node of maximum vibration and attachment of the crowns to the velocity transducers corresponds to an antinode.

21. The replacement system of claim 9 wherein each magnetostrictive element comprises a stack of magnetostrictive leaves received in a bore formed in one end of the crown and brazed thereto.

22. A method for maintaining an ultrasonic dental tool comprising a handpiece having an induction coil disposed about a well and operably connected to a power supply and an insert having a magnetostrictive element disposable in the well, comprising:

using the three-part ultrasonic dental insert of claim 1 in the handpiece;

maintaining a replacement set of insert components comprising the magnetostrictive element, velocity transducer and tip;

upon failure of the insert used in the handpiece, disassembling the insert to remove the failed component(s) thereof and replace the failed component(s) with component(s) from the replacement set.

23. An ultrasonic dental insert for use in a handpiece having an induction coil disposed about a well and operably connected to a power supply, comprising a tip secured to a distal end of a velocity transducer and a head piece of a magnetostrictive stack secured to a proximal end of the velocity transducer, wherein the magnetostrictive stack has one end brazed in a bore formed in a proximal end of the head piece.

* * * * *